(12) United States Patent
Tuma

(10) Patent No.: US 10,390,997 B2
(45) Date of Patent: Aug. 27, 2019

(54) MEDICINAL PRODUCT FOR THE CARE OF AN INDIVIDUAL

(71) Applicant: Gottlieb Binder GmbH & Co. KG, Holzgerlingen (DE)

(72) Inventor: Jan Tuma, Herrenberg (DE)

(73) Assignee: GOTTLIEB BINDER GMBH & CO. KG, Holzgerlingen (DE)

(*) Notice: Subject to any disclaimer, the term of this patent is extended or adjusted under 35 U.S.C. 154(b) by 706 days.

(21) Appl. No.: 13/261,985

(22) PCT Filed: May 28, 2013

(86) PCT No.: PCT/EP2013/001571
§ 371 (c)(1),
(2) Date: Nov. 10, 2014

(87) PCT Pub. No.: WO2013/182279
PCT Pub. Date: Dec. 12, 2013

(65) Prior Publication Data
US 2015/0141895 A1   May 21, 2015

(30) Foreign Application Priority Data
Jun. 8, 2012 (DE) .................. 10 2012 011 422

(51) Int. Cl.
*A61F 13/00* (2006.01)
*A61F 13/02* (2006.01)
(52) U.S. Cl.
CPC .... *A61F 13/00025* (2013.01); *A61F 13/0253* (2013.01); *A61F 2013/00157* (2013.01);
(Continued)

(58) Field of Classification Search
CPC .............................. A61F 13/00–00085; A61F 2013/00089–00357; A61F 13/02–0293;
(Continued)

(56) References Cited

U.S. PATENT DOCUMENTS 4,808,172 A * 2/1989 Murata ............... A61F 13/0203
602/48
2005/0148984 A1* 7/2005 Lindsay ............... A61F 13/5611
604/387
(Continued)

FOREIGN PATENT DOCUMENTS

DE          44 26 315 C1    3/1996
DE   10 2012 204 494 A1    9/2012
(Continued)

*Primary Examiner* — Alireza Nia
*Assistant Examiner* — Michelle J Lee
(74) *Attorney, Agent, or Firm* — Wenderoth, Lind & Ponack, L.L.P.

(57) ABSTRACT

A medicinal product (10) is for the care of an individual having at least one injury such as a burn wound or a skin abrasion, in particular with a large surface area. The product includes at least one functional surface (12, 12', 14) to at least partially cover the injury and/or to fix the medicinal product (10) to the individual. At least one functional surface (12, 12') includes stem parts (18) protruding from the surface. The free end-faces of the stem parts form an adhesion section able to adhere at least partially to the individual and/or to a further functional surface (12'), predominantly by Van der Waals forces.

22 Claims, 4 Drawing Sheets

(52) U.S. Cl.
CPC ............... *A61F 2013/00217* (2013.01); *A61F 2013/00655* (2013.01); *A61F 2013/00838* (2013.01)

(58) Field of Classification Search
CPC ...... A61F 13/06–069; A61F 13/10–148; A61F 13/00357; A61F 13/0296
See application file for complete search history.

(56) References Cited

U.S. PATENT DOCUMENTS

2007/0078365 A1\* 4/2007 Macedo .............. A61F 13/0203
602/52
2009/0216170 A1 8/2009 Robinson et al.
2011/0294931 A1\* 12/2011 Pusel ..................... C08G 18/10
524/133

FOREIGN PATENT DOCUMENTS

EP 2 338 529 A1 6/2011
WO WO 2005/087033 A1 9/2005

\* cited by examiner

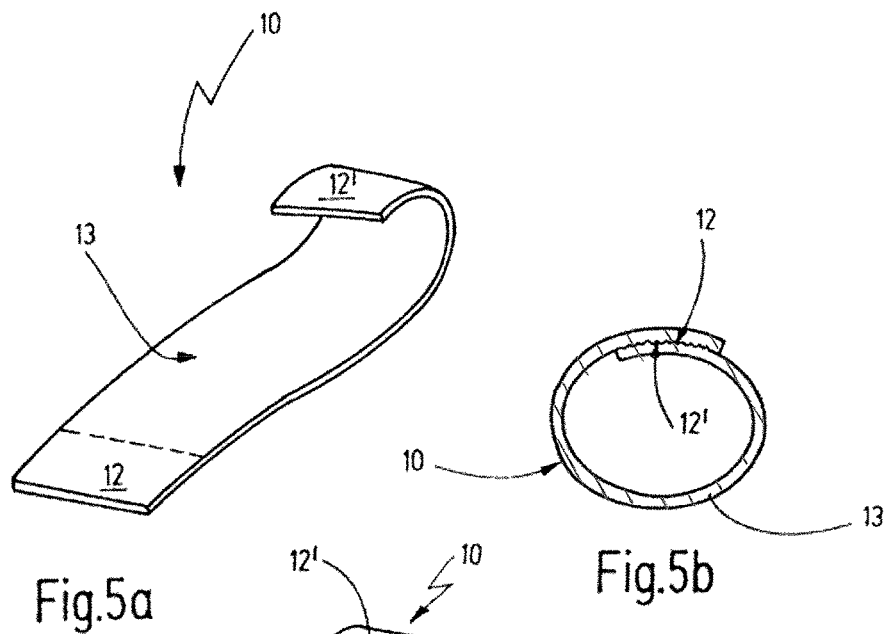
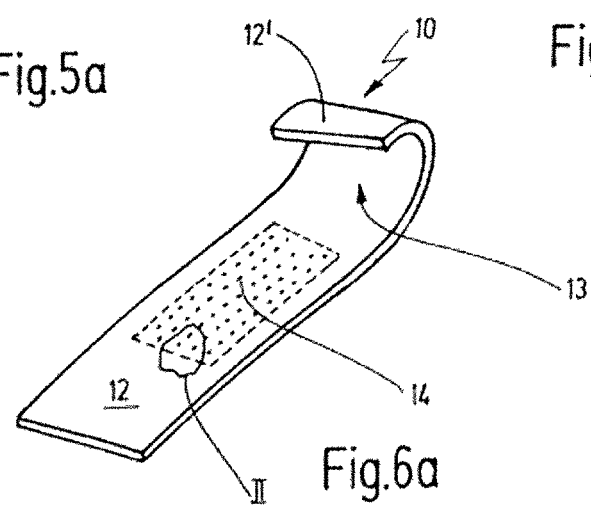
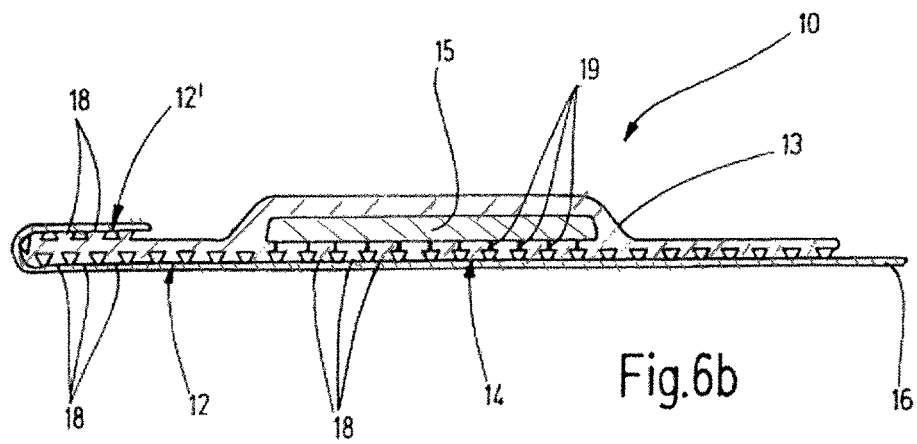

MEDICINAL PRODUCT FOR THE CARE OF AN INDIVIDUAL

FIELD OF THE INVENTION

The invention relates to a medicinal product for the care of an individual having at least one injury such as a burn wound or a skin abrasion, in particular with a large surface area. The product has at least one functional surface for covering the particular injury at least partially and/or for fixing the medicinal product on the individual.

BACKGROUND OF THE INVENTION

Such a medicinal product is known, for example, from EP 1 190 723. The known medicinal product is a wound bandage comprising a carrier film on which an adhesive layer is applied over its entire surface. The adhesive layer includes polyacrylates or rubber and forms an adhesive or functional surface in edge areas of the carrier film for adhesion on the patient. The wound bandage comprises a wound care area based on hydrocolloids as another functional surface to be placed on a wound of the patient. A moist wound healing environment is generated in the wound care area on account of the hydrocolloids, which environment does not allow the wound to dry out and produces an optimal environment for rapid wound healing.

To prevent the moist wound healing environment from drying out and to keep the wound or injury to be treated free of external contamination, a good adhesion of the medicinal product on the individual, in particular on a patient, that suppresses the passage of moisture is necessary. On the other hand, removing the medicinal product from the patient again, for example, when changing the bandage, during which the patient should not be reinjured or exposed to too much pain, is required. In particular, in the case of patients with burn wounds the wound edge areas surrounding the burn wound are very sensitive, so that during the removal of a medicinal product adhered there, in addition to great pain for the patient, a separation of skin layers that were already formed can occur.

SUMMARY OF THE INVENTION

The invention addresses the problem of improving a medicinal product in such a manner that a good fixing, in particular adhesion, of the medicinal product is ensured on the individual via the at least one functional surface, and at the same time a removal of the medicinal product from the patient is made possible that is as painless as possible and free of injury to the patient.

This problem is solved by a medicinal product in accordance with the invention that has at least one functional surface including stem parts projecting from it whose free front-side ends form an adhesion part in such a manner that it can be adhered at least partially on an individual and/or on another functional surface primarily by van der Waals forces.

Van der Waals forces are intermolecular forces named after van der Waals that occur as weak bonding forces between inert atoms and saturated molecules. Whereas during the interaction between atoms only the dispersion forces occur, in the case of molecules, the interactions of induced and of possibly existing permanent dipole moments (orientation effect) are active as additional attraction forces. Van der Waals forces are spoken of by some authors as a synonym for intermolecular forces, but most of them understand van der Waals forces to be such very far-reaching attraction forces between neutral molecules whose energy decreases with the $6^{th}$ power of the molecular interval. The forces are active, for example, in host-guest relationships, in molecular grid crystals, inclusion compounds, molecular compounds and are observable in phenomena of colloidal chemistry, the chemistry of boundary surfaces and of surfaces, etc. (cf. RÖMPPS CHEMIE LEXIKON, $8^{th}$ ed., Franckh'sche Verlagshandlung Stuttgart).

The adhesion of the front-side end of a stem part by van der Waals forces finds a correspondence in nature, for example, in the feet of a gecko that is capable of moving underneath a cover or also along vertically running glass surfaces on account of the shape of its feet. The stems present in an arrangement of millions in a gecko foot are designated in the professional language by "seta" and the individual fibers or individual filaments adjoining the free stem end as "spatula." As a consequence of the fact that, in the medicinal product in accordance with the invention, stem parts are formed projecting opposite the particular functional surface, the adhesion of those stem parts is realized primarily by the cited van der Waals forces, the very good adhesion values of a gecko foot are achieved as a biomechanical model.

The adhesion based on van der Waals forces between the particular functional surface of the medicinal product and, for example, a corresponding contact surface on the body, typically on the skin, of the individual, such as a patient, is so strongly developed that a passage of moisture through the particular adhering functional surface is very largely prevented and the medicinal product can be removed as an entire unit. The van der Waals forces developed on the individual stem part are so low that during the loosening of the functional surface from the contact surface on the body of the patient no undesired injuries, such as the removal of newly formed skin layers, are produced, and the removal of the medicinal product can be carried out with comparatively little pain, optimally without any pain for the patient.

As an alternative to the direct adhesion on the individual, the medicinal product of the invention can be fixed on the individual in such a manner that the particular functional surface adheres to another functional surface. As a result, the medicinal product resting on the appropriate body part of the individual is fixed in the selected position. Stem parts for forming another adhesion part that can be adhered to primarily by van der Waals forces can also be formed on the other functional surface. However, a type of fleece, having at least one looped material but preferably hermaphrodite adhesion elements or another suitable fastening material for cooperating with stem parts of the one functional surface, is formed on the other functional surface. Furthermore, the possibility of adhering on smooth surfaces of the plastic cover band itself exists.

A preferred embodiment of the medicinal product in accordance with the invention comprises a carrier that has at least one functional surface and is formed as a preferably band-shaped surface structure. A carrier with the at least one functional surface, comprising the stem parts, can be very economically produced on a large industrial scale and cut according to the geometrically desired medicinal product. A band-shaped medicinal product can be readily fixed on an individual, such as on a patient, by wrapping the appropriate body part, for example, an arm or a finger. A removable connection of the two functional surfaces, and in this way a removable fastening or fixing of the medicinal product, on the patient can be readily ensured by functional surfaces that comprise at least two stem parts and are provided on the ends of the band-shaped medicinal product, advantageously on the side facing the patient when in use and on the side facing away from the patient when in use. The carrier can be provided, over its entire surface, with a functional surface comprising stem parts on its side facing the patient when in use. However, only partial areas of the carrier can be provided with such functional surface. In particular, the stem parts and/or head parts of the band with a smooth back surface can also directly adhere on account of van der Waals forces.

The medicinal product in accordance with the invention advantageously comprises at least one functional surface for the care of an individual and/or for being placed on the particular injury of an individual, such as on a wound area. Depending on the injury to be cared for, the functional surface comprises substances for producing a moist wound healing environment, for receiving wound secretions, for furthering healing processes in the area of the injury, as a padding, for heating or cooling the injury, etc.

The functional care surface can be surrounded at least partially by at least one functional surface comprising stem parts for forming an adhesion part that adheres on a body part such as on the edge of wound areas surrounding the particular injury. Alternatively, the functional care surface can additionally comprise stem parts for forming an adhesive part that adheres to the particular injury and/or can be covered by a fluid-permeable, preferably perforated, functional layer, which functional layer comprises, on its side facing the particular injury, a functional surface, with stem parts for forming an adhesive part that adheres to the particular injury.

In this manner, the functional surface is functionalized in such a manner that it contributes, in addition to the fastening or fixing of the medicinal product to the individual, to his medicinal care, for example, by medicaments. Such functional surface is, for example, vapor-deposited with gold, provided with a sterilizing medium such as silver particles, or comprises fluid passages for a medicament to be successively applied during the placing of the medicinal product on the wound or on a given body area.

The at least one functional care surface is typically part of a care coating such as a wound coating for the care of a burn wound. The care coating can be fixed on the carrier of the medicinal product and alternatively the functional care surface can be formed directly on the carrier. This arrangement results in the advantage that a ready-for-use medicinal product can be produced and stored under sterile conditions.

Advantageously at least one protective layer, preferably at least one protective film, is provided that covers at least one functional surface and can be pulled off to use the medicinal product. The protective layer prevents an undesired contamination of the medicinal product and an adhering of functional surface(s) comprising the stem parts on third surfaces.

The invention furthermore relates to the use of stem parts projecting opposite a functional surface, the free front ends of which stem parts form such an adhesive part that can be adhered at least partially on an individual and/or on another functional surface, primarily by van der Waals forces, on a medicinal product for the care of an individual with at least one, in particular, large-area wound such as a burn wound or a skin abrasion.

A study carried out on patients with burn wounds on fingers, lower arms and/or upper arms shows that the usage of the medicinal product of the invention distinctly improves the expandability, the color, in particular the reddening, the hydration and the layer thickness of the burnt skin and/or of the burn wound in comparison to traditional medical products. In particular, reduced pain up to no pain for the individual patient was able to be achieved during the taking off or removal of the medicinal product from the patient.

In another preferred embodiment of the medicinal product of the invention, at least the stem parts on the particular functional surface are formed from at least one plastic material. Preferably inorganic and organic elastomers, in particular polyvinyl siloxane, addition-linking silicone elastomers, also in the form of two-component systems, as well as acrylates are used as plastic materials. A plastic material has the advantage that, for example, a flexible carrier can be produced that can be placed on sharply contoured body parts of the individual to be cared for and fixed to them in a manner comparable to a fabric band-aid or a bandage.

Very good adhesion results are achieved if at least 10,000, but preferably 16,000 stem parts, are provided per $cm^2$ on the particular functional surface. The stem parts preferably have a stem body with the form of a rotational hyperboloid. Furthermore, the stem parts can have a head part that is widened in comparison to the stem body, and the front sides or top sides of the widened head parts associated with the adhesion are preferably designed to be substantially planar or slightly convex. As a result of these measures, the adhesion of the contact part formed by the stem parts on a corresponding contact surface on the body of the individual, and the separation of the contact surface, are further improved.

It is sufficient for the adhesion of the corresponding functional surface on the contact surface to place the stem parts flatly, at their free, widened ends, on the contact surface. Preferably the length of the stem parts is selected so that they end via their free ends in a common plane since the van der Waals forces act only over quite a short distance. The particular stem part and/or the particular stem body advantageously has a height of 50 μm to 150 μm, preferably of approximately 90 μm, and a diameter of 10 μm to 40 μm, preferably approximately 30 μm. The head parts, widened in contrast to the stem parts, advantageously have a diameter of 15 μm to 70 μm, preferably approximately 50 μm.

To avoid that the stem parts can bend away from the contact surfaces to be contacted, they have a sufficient intrinsic rigidity. To be able to ensure a good separating behavior, the widened ends or head parts can be connected to the stem body by an appropriate reduction of the diameter in the transitional area to the stem body. In this manner, a type of articulation is produced at the transitional position so that the preferably band-like carrier, with the stem bodies on the appropriate functional surface, is already peeled off and the head part, that is still adhered, follows the peeling-off movement in the sense of a rolling-off movement over the particular articulation, which movement proved to be especially gentle for the patient.

The production of the medicinal product can be designed to be especially favorable if the particular plastic material used is thixotropic. A thixotropic behavior in the sense of the invention should signify the reduction of the structural strength during the shearing loading phase and its more or less rapid but complete reestablishment during the following rest phase. This degradation/reconstruction cycle is a completely reversible process, and thixotropic behavior can be defined as a time-dependent behavior. Furthermore, plastic materials proved to be favorable in which the viscosity measured with a rotary viscosity meter extends from 7,000 to 15,000 mPas, but preferably has a value of approximately 10,000 mPas at a shearing rate of $10 \frac{1}{\text{sec}}$.

In addition, it proved to be advantageous in the sense of a self-cleaning surface to use plastic materials whose contact angle has at least a value greater than 60°, on account of its surface energy, for the wetting with water.

The previously cited features and those cited below can be realized in any combinations in a medicinal product in accordance with the invention when used in accordance with the invention.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure and that are schematic and not true to scale:

FIG. 5a is a perspective view of a medicinal product according to a second exemplary embodiment of the invention;

FIG. 5b is a side view of the medicinal product of FIG. 5a in the position of use;

FIG. 6a is a perspective view of a medicinal product according to a third exemplary embodiment of the invention having the section II; and FIG. 6b is a side view of the medicinal product of FIG. 6a, with a protective film that can be pulled off for using the medicinal product.

DETAILED DESCRIPTION OF THE INVENTION

Figures 1A, 1B:
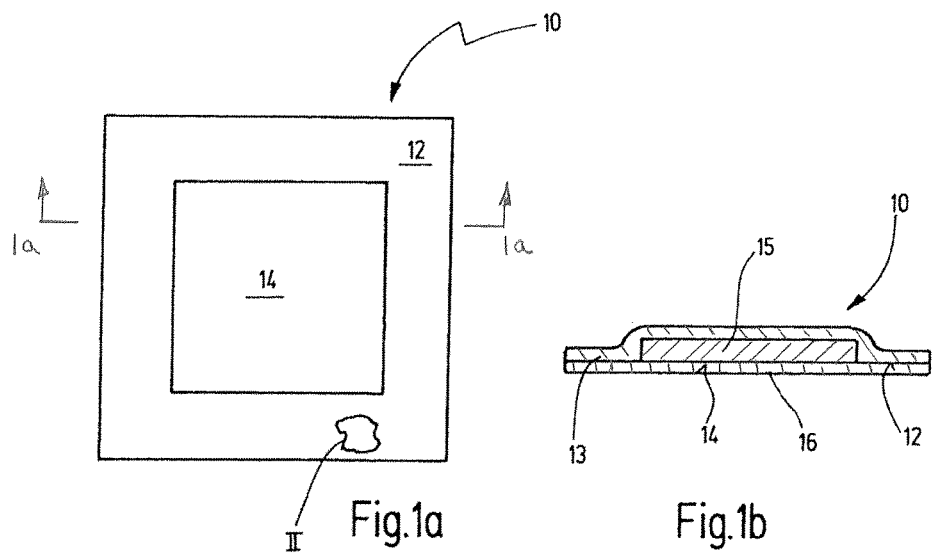
FIGS. 1a and 1b are top plan and side views, respectively, of a medicinal product in accordance with a first exemplary embodiment of the invention.

FIG. 1a shows a top view of a medicinal product 10 that is constructed like a band-aid and comprises a functional surface 12 for adhesion and another functional surface 14 for taking care of the injury to be covered. The functional surfaces are on the side facing the individual, such as a patient to be cared for, during use, or on the side contacting and adhering to this individual. The functional surfaces 12, 14 are constructed to be rectangular, quadratic in the example shown, and are disposed in such a manner, relative to one another, that the one functional surface 12 surrounds the other functional surface 14 and makes possible an adhesion to the individual such as on a contact surface on the body of the patient in edge areas of the medicinal product 10.

The section shown in FIG. 1b through the medicinal product 10 from FIG. 1a shows that the one functional surface 12 is constructed on a carrier 13 and that the other functional surface 14 on a care support 15. The care support 15 can be designed, for example, to receive wound secretions, i.e., absorbent. The medicinal product 10 is constructed in its entirety like a sandwich with a carrier 13 being of a plastic material, the care support 15 and a protective layer covering the functional surfaces 12, 14 in the manner of a protective film 16. The protective film 16 is produced from paper and/or plastic and is removed from the functional surfaces 12, 14 for using the medicinal product 10. The care support 15 is advantageously firmly connected to the carrier 13, for example, adhered. The connection surface can be provided between the carrier 13 and the care support 15 in accordance with the functional surface 12, i.e., with stem parts, so that during a bandage change only the care support 15 has to be replaced and the carrier 13 could be reused.

Figure 2:
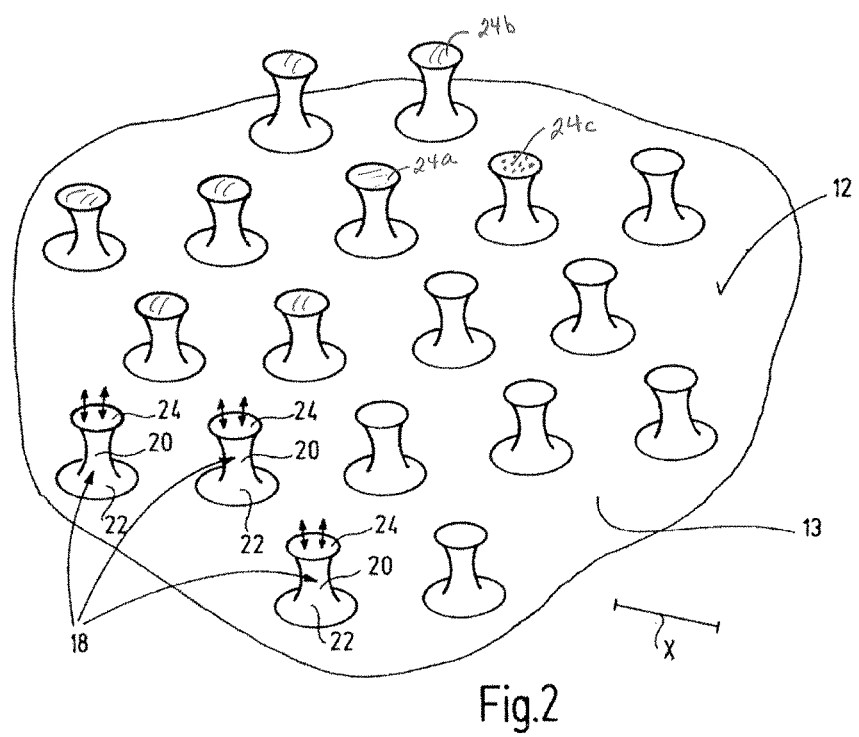
FIG. 2 is a greatly enlarged perspective view of a section II of the medicinal product of FIG. 1a, illustrating the stem parts on a functional surface of the medicinal product.

The dimensions of the medicinal product 10 and of the carrier 13, and accordingly of the care support 15, are multiply selectable, for example, round, elliptical, quadratic, rectangular, triangular, etc. The number and the size of the functional surfaces 12, 14 are selected according to the desired area of use and the requirements placed on the adhesive force. The functional surface 12 provided in the edge area of the medicinal product 10 exhibits a good product adhesion on the body, typically on the skin of the patient and in this way protects the care support 15 for example, from the penetration of contaminations from the outside and from drying out. The microstructure of a section II the functional surface 12 is shown in FIG. 2. The stem parts 18 formed on the functional surface 12 of the carrier 13 project opposite the functional surface 12 and comprise a stem body 20, a foot part connecting the stem body 20 to the functional surface 12 and a head part 24 facing away from the foot part 22 and widened out in comparison to the stem body 20. The front or top side of the particular head part 24 constitutes, as is shown in FIG. 2 with double arrows, the effective surface for forming van der Waals forces with an associated contact surface not shown in FIG. 2, for example, also in the form of a skin surface or a wound surface.

In order to clarify the size relationships of the stem parts 18, in FIG. 2, X designates the length corresponding to the size of approximately 100 μm. Calculated from the functional surface 12 of the carrier 13 to the end of the stem part 18 on the planar top side or front side of the head part 24, each stem part 18 has a height of approximately 100 μm, which corresponds to the size measurement X according to FIG. 2. The planar top sides of the head parts 24 have a diameter of approximately 50 μm and are reduced in the direction of the upper end of the particular stem body 20 to a size of approximately 30 μm. To this extent, a type of undercut is formed between the particular head part 24 and the particular stem body 20 at the location of the transition. The height of the particular head part 24 is approximately 10 μm, and the size of the radial projecting length from the head part 24 to the upper end of the associated stem body 20 is approximately 10 μm. The intervals between the limitations of opposing head parts 24 adjacent to each other are 30 μm to 40 μm. The diameter of the particular stem body 20 is approximately 20 μm to 35 μm.

These size relationships are only exemplary and can be changed in the named size frame, with in any case the particular head part 24 having a planar top side or slightly convex front or top side 24b that makes possible the action of van der Waals forces in as far as the functional surface 12 makes contact with a contact surface of any kind. The contact part can be produced here on an industrial scale. The stem parts 18 can no longer be recognized with the naked eye on account of the nanostructure. Surprisingly, a very reliable, detachable adhesion takes place by the van der Waals forces on account of the construction of stem parts 18.

Figure 3:
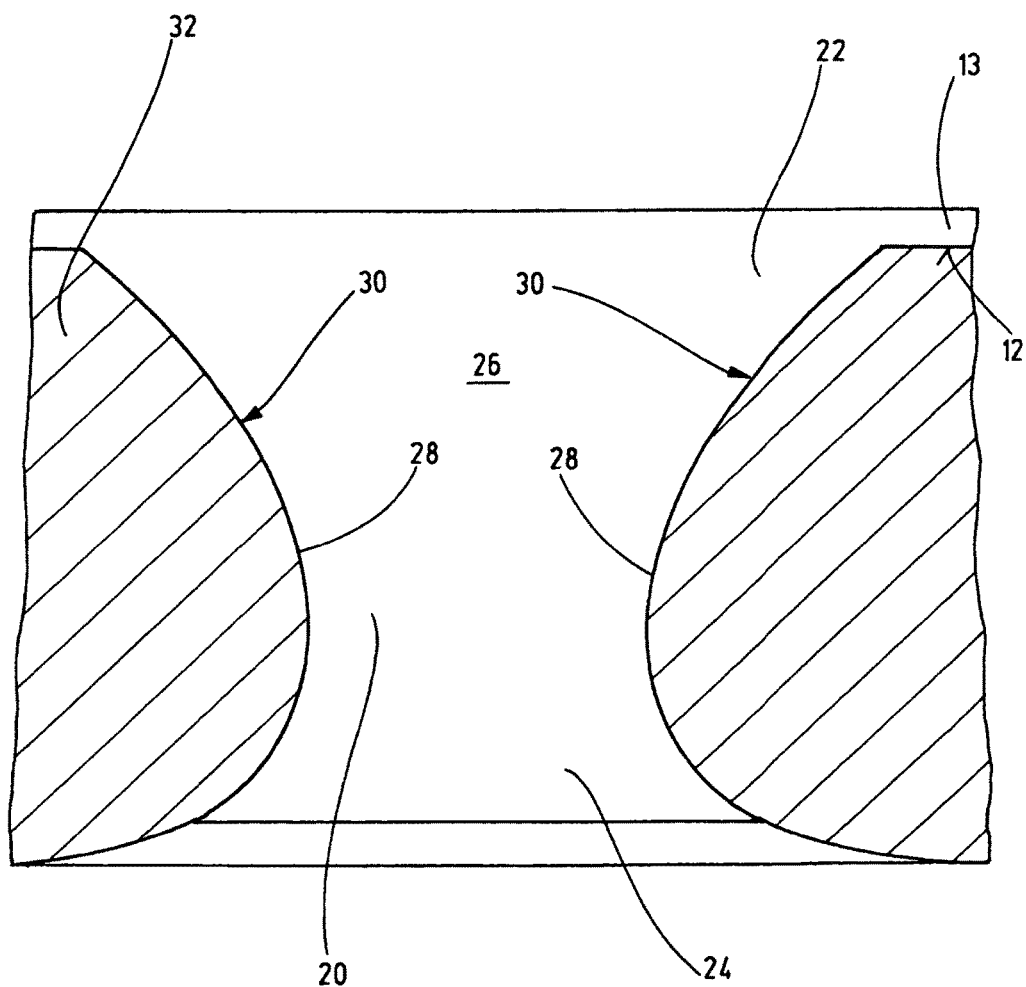
FIG. 3 is a side view in section through a hollow forming space for forming a stem part shown in FIG. 2 together with a head part.

The head parts 24 as well as the stem bodies 20 can be angular, in particular provided with a hexagonal cross-sectional shape. The aspect ratio of each stem part 18 is preferably between 1:3 and 1:5. The shape of the individual stem part 18 can be gathered from FIG. 3, that shows a hollow forming space 26 in a longitudinal section for forming a stem part with a foot part 22, a stem body 20, and a head part widened in comparison to the stem body 20. FIG. 3 shows a longitudinal section of a hollow forming body, wherein the limitation wall 30 shown opposite, in a longitudinal section, has a convex track course. The curvature of the track course is more pronounced in the direction of the head part 24 to be formed than in the direction of the foot part 22, via which the stem body 20 is connected to the carrier 13. The stem part 18 projects away from the functional surface 12 formed on the carrier 13.

The track course of the limitation wall 30 being provided with its greatest curvature above the middle, preferably beginning in the upper third part, viewed from the longitudinal direction of the stem body 20 in the direction of the head part 24 has been proved to be especially advantageous. To form a stem part 18, plastic material is pressed into the hollow forming space 26, comes to rest there and solidifies or hardens there, at least partially. The middle constriction 28, caused by the shape of the rotational hyperboloid, can be continued further in such a manner that, given another constricted position, a type of articulation is produced between the stem body 20 and the head part 24. Such an articulation is advantageous for the van der Waals adhesion system.

Figure 4:
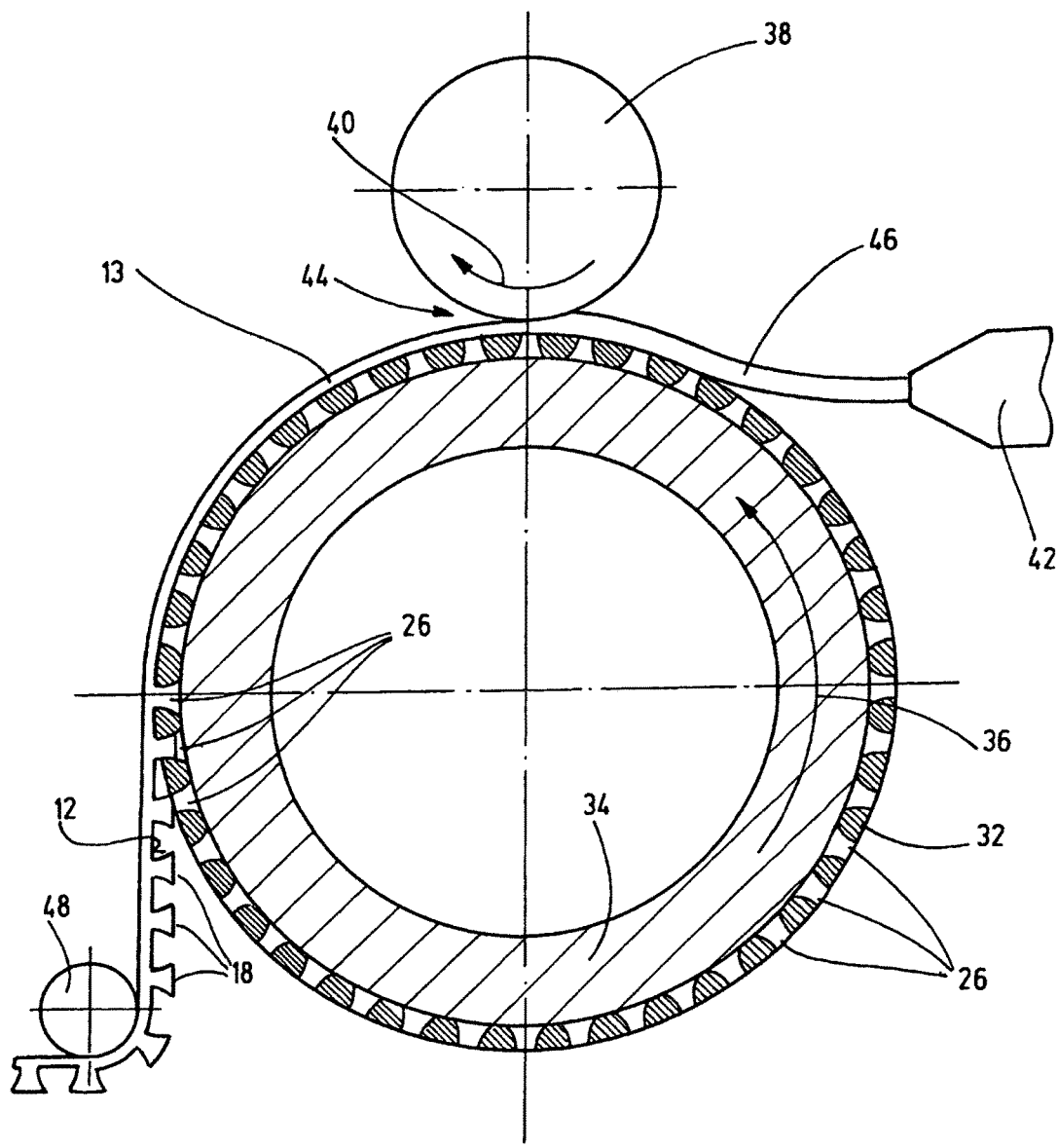
FIG. 4 is a side view in section of a device for producing carrier material for a medicinal product in accordance with the invention, with a forming roller comprising hollow forming spaces according to FIG. 3.

FIG. 4 shows a schematic representation of parts of a device for producing a carrier material 46 for a medicinal product in accordance with the invention and the usage in accordance with the invention. A sieve 32 with a plurality of hollow forming spaces 26 that have the design shown in FIG. 3 is disposed on a forming roller 34 on its outer circumference. The forming roller 34 can rotate counter-clockwise in a first direction of rotation 36. Furthermore, a pressure roller 38 is provided that can rotate clockwise in a second direction of rotation 40 and is disposed in such a manner, relative to the forming roller 34, that a forming gap 44 is formed. A nozzle head 42 is provided as a feed device for plastic, liquid and/or thixotropic plastic material. Carrier material 36 is conducted from the nozzle head 42 to the transport gap 44 and pressed by the pressure applied by the pressure roller 38 on the side facing the forming roller 34 into the hollow forming spaces 26 of the sieve 32. The side of the carrier material 46 associated with the forming roller sets the functional surface 12 on the carrier 13. On the way from the forming gap 44 to a deflection roller 48, the plastic material pressed into the hollow forming spaces 26 hardens at least partially and the correspondingly formed stem parts 18, formed in one piece on the carrier 13, are conducted out of the hollow forming spaces 26.

Carrier material 46 and the carrier 13 with stem parts 18 projecting away from the functional surface 12 can be produced as continuous material by the device shown in FIG. 4 and cut according to the selected size in a cutting device following the deflection roller 48 and not shown in FIG. 4. The carrier material 46 supplied via the nozzle head 42 can be a type of plastic band. The hollow forming spaces 26 on the sieve 32 of the forming roller 34 are disposed according to the design and disposition of the stem parts 18 on the carrier 13. The hollow forming spaces 26 are typically distributed in a uniform manner on the outer circumference of the forming roller 34, with preferably more than 10,000 hollow forming spaces 26 per $cm^2$ on the sieve 32.

The medicinal application using a product according to the depiction according to FIG. 2 as a medicinal product is such a manner that the particular stem bodies 20 come in direct contact, with their preferably widened head parts 24, with the injury, such as a wound area, or body parts and head parts of the patient, in which case the functional surface 12 completely covers the wound area has been proved to be especially advantageous. As soon as the carrier 13 with the functional surface 12 has been formed in the manner of a wrapping bandage, the particular wound area on the body of the patient can also be wrapped so that a complete shielding of the wound area is achieved. As a result of the micro-replicative adhesion of the head parts 24 in the wound area, the carrier band and the carrier 13 can be removed from the wound area without pain, and replaced by a new bandage.

Based on the selected plastic material, the entire product or medicinal product 10 shown in section in FIG. 2 imitates a skin structure to which it is similar in its chemical and physical qualities. A type of artificial skin is then produced that can replace the missing human skin or animal structure, at least for a rather long time. In particular, infections in the wound area are reliably avoided by the cover in accordance with the invention. Instead of widened head parts 24, cylindrically formed stem parts can be split open on their end into individual filaments or spatula 24c for an adhesion of the individual filaments by van der Waals forces.

FIG. 5a shows a top view of another medicinal product 10 formed in the manner of a bandage as a band-like flat article. A band-like carrier 13 has a functional surface 12, 12' on both of its ends. One functional surface 12 is formed on the side of the carrier 13 facing the patient to be cared for, or on the side contacting him when in use. The other functional surface 12' is formed on the side of the carrier 13 facing away from the patient to be cared for, when in use. In the position of use of the medicinal product 10 shown in FIG. 5b, the band-like carrier 13 is wound in a radial direction about a body part of a patient, not shown in FIG. 5b, in such a manner that the end areas of the carrier 13 overlap. The two functional surfaces 12, 12' can then be brought in a position resting on one another. As a result of the position of the functional surfaces 12, 12' in which they rest on one another, a detachable closure is formed on the ends of the carrier 13, as FIG. 5b shows. The medicinal product 10 is fixed on the patient by a radial pressing force.

The functional surface 12 located radially inside, in the position of use of the medicinal product 10, can be designed to cover the entire surface of the corresponding side of the carrier 13. Furthermore, the other functional surface 12', located radially on the outside, in the position of use, can be designed to cover the entire surface on the corresponding side of the carrier 13. As a result, the medicinal product 10 can be flexibly placed on differently sized body parts of the patient and fixed there. Furthermore, in the case of a multiple, or multi-layer, winding around the particular body part with at least partially overlapping layers of the carrier 13, they can be fixed in their particular position. FIG. 5b shows a single winding of the carrier 13 around a body part of the patient. However, multiple windings are also possible.

The other medicinal product 10 shown in FIG. 6a in a perspective view differs from the exemplary embodiment shown in FIG. 5a in that the one functional surface 12, on the side of the carrier facing the patient when in use, is designed to cover the entire surface having a section II as illustrated in FIG. 2. Furthermore, another substantially rectangular functional surface 14 for wound care is formed in a central area of the appropriate side of the carrier 13. The one functional surface 12 and also the other functional surface 14 have the surface structure shown in FIG. 2, with stem parts and head parts (not shown in FIG. 6a) for forming an adhesion primarily by van der Waals forces.

In the section through the medicinal product 10 shown in FIG. 6b, the stem parts 18 are shown on an enlarged scale on the functional surfaces 12, 12',14. Another functional support 15 for wound care is embedded in the carrier 13 and contains, for example, a medicament to be administered on a wound area. The functional surface 14 can be accessed during use on the patient via fluid passages 19 in the carrier 13 and the medicament contained in the care support 15 can be appropriately administered. The fluid passages 19 running from the inner space of the carrier 13, which receives the care support 15, to the surface 14, form, as shown in FIG. 6a, a type of perforation of the carrier 13 in the area of the functional surface 14.

The functional surfaces 12, 12', 14 are protected by a protective film 16 before the use of the medicinal product 10, more precisely before a positioning and fixing on the patent. In the exemplary embodiment shown, a protective film 16 is provided for the functional surfaces 12, 12', 14 on both sides, top and bottom of the carrier 13. Two protective films, that are separate from one another, can be provided on both sides of the carrier 13. On the end opposite the other functional surface 12' the protective film 16 has a projecting length in relation to the carrier 13. As a result of that length, the grasping or holding of the protective film 16 for removing it from the carrier 13 and from the functional surfaces 12, 12' by an attending person, in particular by medical professionals, is facilitated.

In the simplest case, the medicinal functional surface is formed by a carrier band on whose one side the stem parts 18 project. The surface with the stem parts 18 can then be placed on the wound or on the opposite, smooth back side of the carrier band, depending on the nature of the wound. If the carrier band is wrapped around a body part of the individual, the projecting stem parts 18 can sense the adhesion on the smooth back side of the carrier band. To be very pleasant for the particular individual, the degree of the winding force can be very simply adjusted with the band so that winding forces can be obtained, ranging from very loose windings to very firm windings, as needed.

The adhesion of the free stem part ends by van der Waals forces means that the free, front-side end of the particular stem part can sense the adhesion. The possibility also exists of dividing the free end of the cylindrically shaped stem part into a plurality of individual filaments to make the adhesion possible in this manner. However, as already presented, the free head end of the stem part can also be widened from the diameter of the stem part and assume any desired shape, such as polygons, also in a regular shape, cylindrical or elliptical shapes, as well as special shapes such as cloverleaf structures or *chrysanthemum*-like designs. The cited film web can also be constructed to be in several layers and comprise a coating on the side with the stem parts and head parts and also on the back side.

In as far as individuals are concerned with the present application, this concerns not only patients but also animals. On account of the good adhesion behavior of the wound bandage, it can be expected to also be used to its full extent even in the field of aquariums for fish. Furthermore, recent studies have shown that the carrier band can serve almost like a skin replacement. As regards the thin film design, the band can also be sewn on or into the edges of skin parts and tissue parts so that other applications in the field of surgical operations are possible, including in the field of ophthalmology and other plastic surgery. In addition, even internal wound areas and surgical operation areas can be completely covered with a band-like film material. Bleedings can also be effectively controlled.

While various embodiments have been chosen to illustrate the invention, it will be understood by those skilled in the art that various changes and modifications can be made therein without departing from the scope of the invention as defined in the claims.

The invention claimed is:

1. A medicinal product for care of an individual having an injury with a surface area, comprising:
   a carrier;
   a first functional surface on said carrier configured to cover an area adjacent to the injury;
   first stem parts projecting from said first functional surface and having free front-side ends forming adhesion parts adhereable on the individual or a second functional surface primarily by van der Waals forces;
   a functional care surface on said carrier configured to be adhered on the surface area of the injury; and
   second stem parts projecting from said functional care surface and having free front-side ends forming adhesion parts adhereable to the surface area of the injury primarily by van der Waals forces.

2. A medicinal product according to claim 1 wherein each of said stem parts comprises a stem body having a body height of 50 µm to 150 µm and a body diameter of 10 µm to 40 µm.

3. A medicinal product according to claim 2 wherein each of said stem parts comprises a head part having a head diameter of 15 µm to 70 µm.

4. A medicinal product according to claim 3 wherein said head diameter of 50 µm.

5. A medicinal product according to claim 2 wherein said body height is approximately 90 µm; and said body diameter is approximately 30 µm.

6. A medicinal product according to claim 1 wherein said stem parts are formed of an elastomer.

7. A medicinal product according to claim 6 wherein said elastomer is at least one of the group consisting of polyvinyl siloxane, addition-linking silicone elastomer, two component systems or acrylates.

8. A medicinal product according to claim 1 wherein said stem parts are formed of a thixotropic plastic having a viscosity measured with a rotary viscosity meter from 7,000 to 15,000 mPas at a shearing rate of 10 per second.

9. A medicinal product according to claim 8 wherein said viscosity is approximately 10,000 mPas at a shearing rate of 10 per second.

10. A medicinal product according to claim 1 wherein said carrier in said functional care surface is perforated between said second stem parts.

11. A medicinal product according to claim 1 wherein said carrier comprises a band-shaped surface structure.

12. A medicinal product according to claim 1 wherein said first functional surface at least partially surrounds said functional care surface.

13. A medicinal product according to claim 1 wherein said functional care surface comprises a medicinal substance for treating the injury.

14. A medicinal product according to claim 1 wherein a removable protective film extends over said first functional surface and said functional care surface.

15. A medicinal product according to claim 1 wherein
at least 10,000 stem parts per square centimeter are on each of said first functional surface and said functional care surface.

16. A medicinal product according to claim 1 wherein 16,000 stem parts per square centimeter are on each of said first functional surface and said functional care surface.

17. A medicinal product according to claim 1 wherein said stem parts are separated as a spatula on said free front-side ends.

18. A medicinal product according to claim 1 wherein each of said stem parts comprises a stem body having a form of a rotational hyperboloid.

19. A medicinal product according to claim 1 wherein each of said stem parts comprises a stem body and a head part that is wider than the respective stem body, each said head part having a top side providing adhesion and being at least one of substantially planar or slightly convex.

20. A medicinal product according to claim 1 wherein said carrier in said functional care surface has perforations extending through said carrier between said second stem parts and has a medicinal substance on a surface of said carrier opposite said second stem parts that are flowable through said perforations.

21. A method of using a medicinal product for care of an individual having an injury on a part of a body of the individual with a surface area, comprising the steps of:
providing a carrier having first and care functional surfaces configured to cover the injury and having first and second stem parts projecting from said first and care functional surfaces, respectively, said first stem parts forming adhesion parts adhereable on the individual or a second functional surface primarily by van der Waals forces, said second stem parts forming adhesion parts adhereable to the injury primarily by van der Waals forces; and
placing the carrier over the injury with the second stem parts engaging the surface area of the injury.

22. A method according to claim 21 wherein
a medicinal substance on a surface of the carrier opposite the second stem parts flows through perforations extending through the carrier between the stem parts.

* * * * *